(12) United States Patent
Lukacs et al.

(10) Patent No.: US 10,501,535 B2
(45) Date of Patent: Dec. 10, 2019

(54) ANTIBODY TARGETING STEM CELL FACTOR

(71) Applicant: THE REGENTS OF THE UNIVERSITY OF MICHIGAN, Ann Arbor, MI (US)

(72) Inventors: Nicholas W. Lukacs, Brighton, MI (US); Steven L. Kunkel, Ann Arbor, MI (US); Cory Hogaboam, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 15/163,391

(22) Filed: May 24, 2016

(65) Prior Publication Data

US 2016/0257742 A1    Sep. 8, 2016

Related U.S. Application Data

(60) Continuation of application No. 14/328,024, filed on Jul. 10, 2014, now abandoned, which is a continuation-in-part of application No. 15/058,918, filed on Mar. 2, 2016, now Pat. No. 9,790,272, which is a division of application No. 13/937,852, filed on Jul. 9, 2013, now Pat. No. 9,353,178, which is a division of application No. 13/347,459, filed on Jan. 10, 2012, now Pat. No. 8,911,729.

(60) Provisional application No. 61/844,728, filed on Jul. 10, 2013, provisional application No. 61/431,246, filed on Jan. 10, 2011.

(51) Int. Cl.
*C07K 16/24* (2006.01)

(52) U.S. Cl.
CPC .......... *C07K 16/24* (2013.01); *C07K 2317/52* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner | |
| 5,225,539 A | 7/1993 | Winter | |
| 5,641,870 A | 6/1997 | Rinderknecht | |
| 5,731,168 A | 3/1998 | Carter | |
| 5,885,962 A | 3/1999 | Lu et al. | |
| 6,207,417 B1 | 3/2001 | Zsebo et al. | |
| 6,506,559 B1 | 1/2003 | Fire | |
| 7,144,731 B2 | 12/2006 | Zseebo et al. | |
| 7,285,640 B2 | 10/2007 | Takeuchi et al. | |
| 7,582,297 B2 | 9/2009 | Reed | |
| 7,893,036 B2 | 2/2011 | Zamore | |
| 8,278,067 B2 | 10/2012 | Longley | |
| 8,911,729 B2 | 12/2014 | Lukacs et al. | |
| 9,353,178 B2 | 5/2016 | Lukacs et al. | |
| 2003/0194405 A1 | 10/2003 | Takeuchi et al. | |
| 2005/0112698 A1 | 5/2005 | Neben | |
| 2005/0136057 A1 | 6/2005 | Sato et al. | |
| 2005/0282233 A1 | 12/2005 | Eriksson et al. | |
| 2007/0253951 A1 | 11/2007 | Ng et al. | |
| 2008/0025958 A1 | 1/2008 | Hannon | |
| 2008/0200420 A1 | 8/2008 | Zamore | |
| 2008/0247951 A1 | 10/2008 | Koch et al. | |
| 2008/0269147 A1 | 10/2008 | Tuschl | |
| 2008/0305074 A1 | 12/2008 | Zsebo et al. | |
| 2009/0123974 A1 | 5/2009 | Gantier et al. | |
| 2010/0305003 A1 | 12/2010 | Tang | |

FOREIGN PATENT DOCUMENTS

| | | |
|---|---|---|
| EP | 125023 | 11/1984 |
| EP | 171496 | 2/1986 |
| EP | 173494 | 3/1986 |
| EP | 184187 | 6/1986 |
| EP | 0676470 A1 | 10/1995 |
| WO | 198601533 | 3/1989 |
| WO | 198702671 | 8/2003 |
| WO | 2003070966 A2 | 8/2003 |
| WO | 2005038054 A1 | 4/2005 |
| WO | 2005054270 | 6/2005 |
| WO | 2005068503 A2 | 7/2005 |
| WO | 2006066048 | 6/2006 |
| WO | 2007049017 A2 | 5/2007 |
| WO | 2008006369 | 1/2008 |
| WO | 2008043753 | 4/2008 |
| WO | 2008051306 | 5/2008 |
| WO | 2009117769 A1 | 10/2009 |
| WO | 2011016238 A1 | 2/2011 |

OTHER PUBLICATIONS

Andre et al., "c-kit mRNA expression in human and murine hematopoietic cell lines." Oncogene. Aug. 1989; 4(8):1047-9.
Aono et al., "Imatinib as a novel antifibrotic agent in bleomycin-induced pulmonary fibrosis in mice." Am J Respir Crit Care Med. Jun. 1, 2005; 171(11)1279-85.
Beidler et al., "Cloning and high level expression of a chimeric antibody with specificity for human carcinoembryonic antigen." J Immunol. Dec. 1, 1988; 141(11):4053-60.
Berlin et al., "Inhibition of SCF attenuates peribronchial remodeling in chronic cockroach allergen-induced asthma." Lab Invest. Jun. 2006;86(6):557-65.
Better et al., "*Escherichia coli* secretion of an active chimeric antibody fragment." nce. May 20, 1988; 240(4855):1041-3.
Bohula et al., "The efficacy of small interfering RNAs targeted to the type 1 insulin-like growth factor receptor (IGF1R) is influenced by secondary structure in the IGF1R transcript." J Biol Chem. May 2, 2003;278(18):15991-7.

(Continued)

*Primary Examiner* — Christine J Saoud
(74) *Attorney, Agent, or Firm* — Casimir Jones S.C.; Thomas Isenbarger

(57) ABSTRACT

Provided herein are methods, compositions, and uses relating to inhibitors of stem cell factor. For example, provided herein are antibodies targeting stem cell factor and methods for treating fibrotic and tissue remodeling diseases.

7 Claims, 2 Drawing Sheets

Specification includes a Sequence Listing.

(56) References Cited

OTHER PUBLICATIONS

Brennan et al., "Preparation of bispecific antibodies by chemical recombination of monoclonal immunoglobulin G1 fragments." Science. Jul. 5, 1985;229(4708):81-3.
Brummelkamp et al., "A system for stable expression of short interfering RNAs in mammalian cells." Science. Apr. 19, 2002;296(5567):550-3.
Caplen et al., "Specific inhibition of gene expression by small double-stranded RNAs in invertebrate and vertebrate systems." Proc Natl Acad Sci U S A. Aug. 14, 2001;98(17)9742-7.
Clackson et al., "Making antibody fragments using phage display libraries." Nature. Aug. 15, 1991; 352(6336):624-8.
Coloma et al., "Primer design for the cloning of immunoglobulin heavy-chain leader-variable regions from mouse hybridoma cells using the PCR." Biotechniques. Aug. 1991;11(2):152-4, 156.
Distler et al, "Imatinib mesylate reduces production of extracellular matrix and prevents development of experimental dermal fibrosis." Arthritis Rheum. Jan. 2007; 56(1):311-22.
Dolgachev et al., "Role of Stem Cell factor and bone marrow-derived fibroblasts in airway remodeling." Am. J. Pathol 2009, 174(2):390-400.
El Kossi et al., "Stem cell factor and crescentic glomerulonephritis." Am J Kidney Dis. Apr. 2003; 41(4):785-95.
Elbashir et al., "Duplexes of 21-nucleotide RNAs mediate RNA interference in cultured mammalian cells." Nature. May 24, 2001;411(6836):494-8.
Elbashir et al., "Functional anatomy of siRNAs for mediating efficient RNAi in *Drosophila melanogaster* embryo lysate." EMBO J. Dec. 3, 2001;20(23):6877-88.
Elbashir et al., "RNA interference is mediated by 21- and 22-nucleotide RNAs." Genes Dev. Jan. 15, 2001;15(2):188-200.
El-Koraie et al., "Role of stem cell factor and mast cells in the progression of chronic glomerulonephritides." Kidney Int. Jul. 2001; 60(1):167-72.
GenBank Accession No. NG_012098, *Homo sapiens* KIT ligand (KITLG), RefSeqGene on chromosome 12.
GenBank Accession No. NM_000899, *Homo sapiens* KIT ligand (KITLG), transcript variant b, Mrna.
GenBank Accession No. NM_003994, *Homo sapiens* KIT ligand (KITLG), transcript variant a, Mrna.
GenBank Accession No. NP_000890, kit ligand isoform b precursor [*Homo sapiens*].
GenBank Accession No. NP_003985, kit ligand isoform a precursor [*Homo sapiens*].
GenBank Direct Submission. B61190 titled "mast cell growth factor, short form precursor-human" (PRI Jul. 21, 2000) <http://www.ncbi.nlm.nih.gov/protein/B61190?report=genpept./.
Goding, Monoclonal Antibodies: Principles and Practice, Academic Press, 1986.
Gruber et al., "Efficient tumor cell lysis mediated by a bispecific single chain antibody expressed in *Escherichia coli*." J Immunol. Jun. 1, 1994;152(11):5368-74.
Harlow & Lane, "Antibodies: A Laboratory Manual" Copld Spring Harbor Laboratory Press, Cold Spring Harbor, NY, 1988.
Holen et al., "Positional effects of short interfering RNAs targeting the human coagulation trigger Tissue Factor." Nucleic Acids Res. Apr. 15, 2002;30(8):1757-66.
Huang et al., "The hematopoietic growth factor KL is encoded by the Sl locus and is the ligand of the c-kit receptor, the gene product of the W locus." Cell. Oct. 5, 1990;63(1):225-33.
Huse et al., "Generation of a large combinatorial library of the immunoglobulin repertoire in phage lambda." Science. Dec. 8, 1989;246(4935)1275-81.
Jones et al., "Replacing the complementarity-determining regions in a human antibody with those from a mouse." Nature. May 29-Jun. 4, 1986; 321(6069):522-5.
Kohler et al., "Continuous cultures of fused cells secreting antibody of predefined specificity." Nature. Aug. 7, 1975;256(5517):495-7.

Kostelny et al., "Formation of a bispecific antibody by the use of leucine zippers." J Immunol. Mar. 1, 1992;148(5):1547-53.
Kozbor et al., "The Production of Monoclonal Antibodies from Human lymphocytes." Immunology Today. 1983, 4:72-79.
Kretschmer-Kazemi & Sczakiel, "The activity of siRNA in mammalian cells is related to structural target accessibility: a comparison with antisense oligonucleotides." Nucleic Acids Res. Aug. 1, 2003;31(15):4417-24.
Larrick et al., :PCR Amplification of Antibody Genes. Methods: Companion to Methods in Enzymology 1991, 2:106.
Liu et al., "Chimeric mouse-human IgG1 antibody that can mediate lysis of cancer cells." Proc Natl Acad Sci U S A. May 1987;84(10):3439-43.
Liu et al., "Production of a mouse-human chimeric monoclonal antibody to CD20 with potent Fc-dependent biologic activity." J Immunol. Nov. 15, 1987;139(10):3521-6.
Marks et al., "By-passing immunization. Human antibodies from V-gene libraries displayed on phage." J Mol Biol. Dec. 5, 1991;222(3):581-97.
Martin et al., "Primary structure and functional expression of rat and human stem cell factor DNAs." Cell. Oct. 5, 1990; 63(1):203-11.
McCafferty et al., "Phage antibodies: filamentous phage displaying antibody variable domains."Nature. Dec. 6, 1990; 348(6301):552-4.
Milstein et al., "Hybrid hybridomas and their use in immunohistochemistry." Nature. Oct. 6-12, 1983;305(5934):537-40.
Morimoto et al., "Single-step purification of F(ab')2 fragments of mouse monoclonal antibodies (immunoglobulins G1) by hydrophobic interaction high performance liquid chromatography using TSKgel Phenyl-5PW." vol. 24, Issues 1-2, 1992, pp. 107-117.
Morrison, "Transfectomas provide novel chimeric antibodies." Science. Sep. 20, 1985;229(4719):1202-7.
Nishimura et al., "Recombinant human-mouse chimeric monoclonal antibody specific for common acute lymphocytic leukemia antigen." Cancer Res. Feb. 15, 1987;47(4):999-1005.
Oi et al., "Chimeric Antibodies." BioTechniques 1986, 4:214.
Orlandi et al., "Cloning immunoglobulin variable domains for expression by the polymerase chain reaction." Proc Natl Acad Sci U S A. May 1989;86(10):3833-7.
Orr-Urtreger et al., "Developmental expression of c-kit, a proto-oncogene encoded by the W locus." Development. Aug. 1990; 109(4):911-23.
Overhoff et al., "Local RNA target structure influences siRNA efficacy: a systematic global analysis." J Mol Biol. May 13, 2005;348(4):871-81.
Pluckthun, "Antibodies from *Escherichia coli*." in the Phamacology of Monoclonal Antibodies, M. Rosenberg and G.P. Moore Eds., (Springer Verlag, Berlin 1994), 113:269-315.
Powell et al., "Epithelial cells and their neighbors I. Role of intestinal myofibroblasts in development, repair, and cancer." Am J Physiol Gastrointest Liver Physiol. Jul. 2005; 289(1):G2-7.
Powell et al., "Myofibroblasts. II. Intestinal subepithelial myofibroblasts." Am J Physiol. Aug. 1999; 277(2 Pt 1): C183-201.
Remington's pharmaceutical sciences, 17th ed. Edited by Alfonso R. Gennaro. Mack Publishing Co., 20th and Northampton Streets, Easton, PA 18042. 1985.
S.P.C. Cole, D. Kozbor and J.C. Roder. "The EBV-hybridoma technique and its application to human lung cancer." In, Monoclonal Antibodies and Cancer Therapy (vol. 27, UCLA Symposia on Molecular and Cellular Biology, New Series) (eds. R.A. Reisfeld and S.Sell), pp. 77-96, Alan R. Liss, Inc. N.Y., 1985.
Sastry et al., "Cloning of the immunological repertoire in *Escherichia coli* for generation of monoclonal catalytic antibodies: construction of a heavy chain variable region-specific cDNA library." Proc Natl Acad Sci U S A. Aug. 1989; 86(15):5728-32.
Schubert et al., "Local RNA target structure influences siRNA efficacy: systematic analysis of intentionally designed binding regions." J Mol Biol. May 13, 2005;348(4):883-93.
Shalaby et al., "Development of humanized bispecific antibodies reactive with cytotoxic lymphocytes and tumor cells overexpressing the HER2 protooncogene." J Exp Med. Jan. 1, 1992;175(1):217-25.

(56) References Cited

OTHER PUBLICATIONS

Shaw et al., "Mouse/human chimeric antibodies to a tumor-associated antigen: biologic activity of the four human IgG subclasses." J Natl Cancer Inst. Dec. 7, 1988;80(19):1553-9.
Sohail et al., "Antisense oligonucleotides selected by hybridisation to scanning arrays are effective reagents in vivo." Nucleic Acids Res. May 15, 2001;29(10):2041-51.
Stumpp & Amstutz, "DARPins: a true alternative to antibodies." Curr Opin Drug Discov Devel. Mar. 2007;10(2):153-9.
Sun et al., "Chimeric antibody with human constant regions and mouse variable regions directed against carcinoma-associated antigen 17-1A."Proc Natl Acad Sci U S A. Jan. 1987;84(1):214-8.
Suresh et al., "Bispecific monoclonal antibodies from hybrid hybridomas." Methods Enzymol. 1986;121:210-28.
Traunecker et al., "Bispecific single chain molecules (Janusins) target cytotoxic lymphocytes on HIV infected cells." EMBO J. Dec. 1991;10(12):3655-9.
Tuschl & Borkhardt, "Small interfering RNAs: a revolutionary tool for the analysis of gene function and gene therapy." Mol Interv. Jun. 2002;2(3):158-67.
Tuschl et al., "Targeted mRNA degradation by double-stranded RNA in vitro." Genes Dev. Dec. 15, 1999;13(24):3191-7.
Verhoeyen et al., "Reshaping human antibodies: grafting an antilysozyme activity" Science Mar. 25, 1988: 1534-1536.
Vittal et al., "Effects of the protein kinase inhibitor, imatinib mesylate, on epithelial/mesenchymal phenotypes: implications for treatment of fibrotic diseases." J Pharmacol Exp Ther. Apr. 2007; 321(1):35-44.
Vuorinen et al., "Imatinib mesylate inhibits fibrogenesis in asbestos-induced interstitial pneumonia." Exp Lung Res. Sep. 2007;33(7):357-73.
Williams et al., "Identification of a ligand for the c-kit proto-oncogene." Cell. Oct. 5, 1990; 63(1):167-74.
Wood et al., "The synthesis and in vivo assembly of functional antibodies in yeast." Nature. Apr. 4-10, 1985;314(6010):446-9.
Zapata et al., "Engineering linear F(ab')2 fragments for efficient production in *Escherichia coli* and enhanced antiproliferative activity." Protein Eng. Oct. 1995;8(10):1057-62.
Zsebo et al., "Identification, purification, and biological characterization of hematopoietic stem cell factor from buffalo rat liver—conditioned medium." Cell. Oct. 5, 1990; 63(1):195-201.
Documents Cited During Prosecution of U.S. Appl. No. 13/347,459, filed Jan. 10, 2012. Now U.S. Pat. No. 8,911,729, Issued Dec. 16, 2014.
Gagari et al., "Expression of stem cell factor and its receptor, c-kit, in human oral mesenchymal cells." Eur J Oral Sci. Oct. 2006;114(5):409-15.
GenBank Accession No. AF400436_1, published Aug. 21, 2001, Retrived Oct. 21, 2015, 1 page.
GenBank Accession No. CAH18078, published Oct. 7, 2008, Retrieved Oct. 21, 2015, 2 page.
International Preliminary Report on Patentability, PCT/US2012/020782, dated Jul. 6, 2012, 12 pages.
International Preliminary Report on Patentability, PCT/US2014/046138, dated Dec. 15, 2014, 18 pages.
Majumdar et al., "Identification and mutation of primary and secondary proteolytic cleavage sites in murine stem cell factor cDNA yields biologically active, cell-associated protein." J Biol Chem. Jan. 14, 1994;269(2):1237-42.
Langley et al., "Properties of variant forms of human stem cell factor recombinantly expressed in *Escherichia coli*." Arch Biochem Biophys. May 15, 1994;311(1):55-61.

Figure 1

Heavy chain: DNA sequence (402 bp) (SEQ ID NO. 1)

Leader sequence-FR1-CDR1-FR2-CDR2-FR3-CDR3-FR4

ATGGACAGGCTTACTTCTTCATTCCTGCTGCTGATTGTCCCTGCATATGTCTTATCCAAGTTTCTC
                                                              |CDR1|
                                        |————————FR1————————|

TAAAGAGTCTGGCCCTGGGATATTGAGGCCTTCACAGACCCTCATTCTGACTTGTTCTTTCTCTGG
|CDR1|  |————————————————FR1————————————————|

GTTTTCACTGAGTACTCTGGTGTGGGCTGGATTCGTCAGCCTTCAGGGAAGGGTCTGGAG
     |——FR2——|              |————————CDR2————————|  |—FR3—|

TGGCTGGCACATTTGGTGGATGGAGAAGTCCTATAACCCATCCCTGAAGATGGACTACAGATACTGC
|————————CDR2————————|              |————————FR3————————|

TCTCCAAGGATGCCTCCCGAGACGTTTCCTCAAGATCACCAGATTCAGTCAAGGAATTTCAGTCACCGTCTCCTCA
     |—FR3—|                              |————CDR3————|  |———FR4———|

CACTTACTTCTGCGCTCGAAGCGGTCTGGACTACTGG
|———FR4———|

Heavy chain: Amino acids sequence (134 AA) (SEQ ID NO. 2)

Leader sequence-FR1-CDR1-FR2-CDR2-FR3-CDR3-FR4

MDRLTSSFLLLIVPAYVLSQVSLKESGPGILRPSQTLILTCSFSGFSLSTSGMGVGWIRQPSGKGLE
                   |————————FR1————————|              |—CDR1—|  |—FR2—|

WLAHIWWDDEKSYNPSLKSRLTISKDASRDQVFLKITNVDTTDTATYFCARSGLDWGQGISVTVSS
|————CDR2————|  |————————FR3————————|              |CDR3|  |—FR4—|

Figure 1 Continued

Light chain: DNA sequence (402 bp) (SEQ ID NO. 3)

Leader sequence-FR1-CDR1-FR2-CDR2-FR3-CDR3-FR4

ATGGCTTGGACTCCTCTCTTCTTCTTCTTCTTGTTCTCAGGTTCTTTCTCCAACCTGTCC
TCACTCAGTCATCTCAGCCTGTCCTGACCCAGAGCCTCAGCAGCCTCAGCCTCAGCCTCAGCCAAAATCACGTGCACCTTGAGTAG
TCAGCACAGGAGTACACCATTGATGGAATGGTATCAGCAACAGCCACTCAAGCCTAAGTAGTGATG
CAACTTAAGAGATGGAAGTCACTTAATCCATTGCCAACACCCAGCTGAAGATGAAGAATGTACATCCAGCT
CTGGTGCTGATGATACAATTCAGGAACAATTTGTGTATGTTTTCGGCGGTGGAACCAAAGTCACTGTCCTC

Light chain: Amino acids sequence (134 AA) (SEQ ID NO. 4)

Leader sequence-FR1-CDR1-FR2-CDR2-FR3-CDR3-FR4

MAWTPLFFFVLHCSGSFSQPVLTQSSASFSLGASAKITCTLSSQHRTYTIEWYQQQPLKPPKYVM
ELKRDGSHRTGDGIPDRFSGSSSGADRYLTIANIQPEDEAMYICGADDTIQEQFVYVFGGGTKVTVL

SEQUENCE LISTING

<160> NUMBER OF SEQ ID NOS: 4

<210> SEQ ID NO 1
<211> LENGTH: 402
<212> TYPE: DNA
<213> ORGANISM: Homo sapiens

<400> SEQUENCE: 1

```
atggacaggc ttacttcttc attcctgctg ctgattgtcc ctgcatatgt cttatcccaa      60
gtttctctaa aagagtctgg ccctgggata ttgaggccct cacagaccct cattctgact     120
tgttctttct ctgggttttc actgagtact tctggtatgg gtgtgggctg gattcgtcag     180
ccttcaggga agggtctgga gtggctggca cacatttggt gggatgatga gaagtcctat     240
aacccatccc tgaagagccg gctcacgatc tccaaggatg cctcccgaga ccaggttttc     300
ctcaagatca ccaatgtgga cactacagat actgccactt acttctgtgc tcgaagcggc     360
ttggactact ggggtcaagg aatttcagtc accgtctcct ca                        402
```

<210> SEQ ID NO 2
<211> LENGTH: 134
<212> TYPE: PRT
<213> ORGANISM: Homo sapiens

<400> SEQUENCE: 2

```
Met Asp Arg Leu Thr Ser Ser Phe Leu Leu Ile Val Pro Ala Tyr
1               5                   10                  15

Val Leu Ser Gln Val Ser Leu Lys Glu Ser Gly Pro Gly Ile Leu Arg
            20                  25                  30

Pro Ser Gln Thr Leu Ile Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Glu Lys Ser Tyr
65                  70                  75                  80

Asn Pro Ser Leu Lys Ser Arg Leu Thr Ile Ser Lys Asp Ala Ser Arg
                85                  90                  95

Asp Gln Val Phe Leu Lys Ile Thr Asn Val Asp Thr Thr Asp Thr Ala
            100                 105                 110

Thr Tyr Phe Cys Ala Arg Ser Gly Leu Asp Tyr Trp Gly Gln Gly Ile
        115                 120                 125

Ser Val Thr Val Ser Ser
    130
```

<210> SEQ ID NO 3
<211> LENGTH: 402
<212> TYPE: DNA
<213> ORGANISM: Homo sapiens

<400> SEQUENCE: 3

```
atggcctgga ctcctctctt cttcttcttt gttcttcatt gctcaggttc tttctcccaa      60
cctgtgctca ctcagtcatc ttcagcctct ttctccctgg gagcctcagc aaaaatcacg     120
tgcaccttga gtagtcagca caggacgtac accattgaat ggtatcagca acagccactc     180
aagcctccta gtatgtgat ggaacttaag agagatggaa gtcacagaac aggtgatggg     240
attcctgatc gcttctctgg atccagctct ggtgctgatc gctacctaac cattgccaac     300
```

-continued

```
atccagcctg aagatgaagc aatgtacatc tgtggtgctg atgatacaat tcaggaacaa       360
tttgtgtatg ttttcggcgg tggaaccaaa gtcactgtcc tc                          402
```

<210> SEQ ID NO 4
<211> LENGTH: 134
<212> TYPE: PRT
<213> ORGANISM: Homo sapiens

<400> SEQUENCE: 4

```
Met Ala Trp Thr Pro Leu Phe Phe Phe Val Leu His Cys Ser Gly
1               5                  10                  15

Ser Phe Ser Gln Pro Val Leu Thr Gln Ser Ser Ser Ala Ser Phe Ser
            20                  25                  30

Leu Gly Ala Ser Ala Lys Ile Thr Cys Thr Leu Ser Ser Gln His Arg
        35                  40                  45

Thr Tyr Thr Ile Glu Trp Tyr Gln Gln Pro Leu Lys Pro Lys
    50                  55                  60

Tyr Val Met Glu Leu Lys Arg Asp Gly Ser His Arg Thr Gly Asp Gly
65                  70                  75                  80

Ile Pro Asp Arg Phe Ser Gly Ser Ser Ser Gly Ala Asp Arg Tyr Leu
                85                  90                  95

Thr Ile Ala Asn Ile Gln Pro Glu Asp Glu Ala Met Tyr Ile Cys Gly
            100                 105                 110

Ala Asp Asp Thr Ile Gln Glu Gln Phe Val Tyr Val Phe Gly Gly Gly
        115                 120                 125

Thr Lys Val Thr Val Leu
    130
```

ANTIBODY TARGETING STEM CELL FACTOR

The present application is a continuation of, and claims priority to, U.S. patent application Ser. No. 14/328,024, filed Jul. 10, 2014, which claims priority to U.S. Provisional Patent Application Ser. No. 61/844,728, filed Jul. 10, 2013; and is a continuation-in-part of, and claims priority to, U.S. patent application Ser. No. 15/058,918, filed Mar. 2, 2016, which is a divisional of U.S. patent application Ser. No. 13/937,852, filed Jul. 9, 2013, which is a divisional of U.S. patent application Ser. No. 13/347,459, filed Jan. 10, 2012, now U.S. Pat. No. 8,911,729, issued on Dec. 16, 2014, which claims priority to U.S. Provisional Patent Application Ser. No. 61/431,246, filed on Jan. 10, 2011, the disclosures of each of which is herein incorporated by reference in its entirety.

FIELD OF INVENTION

Provided herein are methods, compositions, and uses relating to antibody inhibitors of stem cell factor. For example, provided herein are antibodies targeting stem cell factor and methods for treating fibrotic and tissue remodeling diseases.

BACKGROUND

Diseases involving tissue remodeling and fibrosis are a leading cause of death worldwide. Nearly 45 percent of all natural deaths in the western world are attributable to some type of chronic fibroproliferative disease and the associated health care costs are in the billions of dollars. Tissue remodeling is the reorganization or renovation of existing tissues, which can either change the characteristics of a tissue (e.g., blood vessel remodeling) or participate in establishing the dynamic equilibrium of a tissue (e.g., bone remodeling). Fibrosis is the formation or development of excess fibrous connective tissue in an organ or tissue as a reparative or reactive process, as opposed to formation of fibrous tissue as a normal constituent of an organ or tissue. Fibrosis affects nearly all tissues and organ systems, and fibrotic tissue remodeling can influence cancer metastasis and accelerate chronic graft rejection in transplant recipients. Diseases in which fibrosis is a major cause of morbidity and mortality include the interstitial lung diseases, liver cirrhosis, kidney disease, heart disease, and systemic sclerosis, among others.

Stem cell factor (SCF) and its receptor c-Kit have been implicated in fibrotic and tissue remodeling diseases (El-Koraie, et al., Kidney Int. 60: 167 (2001); Powell, et al., Am. J. Physiol. 289: G2 (2005); El Kossi, et al., Am. J. Kidney Dis. 41: 785 (2003); Powell, et al., Am. J. Physiol. 277: C183 (1999)). c-Kit is a type III receptor-tyrosine kinase that is present in many cell types (Orr-Urtreger et al., Development 109: 911 (1990)). It is also expressed in the early stages of differentiation (Andre et al., Oncogene 4: 1047 (1989)) and certain tumors exhibit elevated expression of c-kit. SCF is a ligand specific for the c-Kit receptor kinase. Binding causes dimerization of c-Kit and activation of its kinase activity. SCF was first isolated from the supernatant of murine fibroblasts. At the time, SCF was called mast cell growth factor (MGF) (Williams et al., Cell 63: 167 (1990)) or hematopoietic growth factor KL (Kit ligand) (Huang et al., Cell 63: 225 (1990)). A homologue was subsequently isolated from rat liver cells and designated stem cell factor (SCF) (Zsebo et al., Cell 63: 195 (1990)). The corresponding human protein is designated variously as SCF, MGF, or Steel Factor (SF) (Cell 63: 203 (1990)).

Previous studies have suggested that an inhibitor of c-Kit receptor tyrosine kinase can significantly inhibit aberrant tissue fibrosis (see, e.g., Aono, Am. J. Respir. Crit. Care Med. 171: 1279 (2005); Vuorinen, et al., Exp. Lung Res. 33: 357 (2007); Vittal, et al., J. Pharmacol. Exp. Ther. 321: 35 (2007); Distler, et al., Arthritis Rheum 56: 311 (2007)). However, this inhibitor has several disadvantages. It needs to be given systemically by oral administration, it has some toxicity associated with its use, and the compound must be delivered intracellularly for efficacy. Consequently, alternative therapies are needed.

SUMMARY

Provided herein are methods, compositions, and uses relating to inhibitors of stem cell factor. For example, provided herein are antibodies targeting stem cell factor and methods for treating fibrotic and tissue remodeling diseases as well as for research and diagnostic uses.

Embodiments of the present invention provide an isolated recombinant monoclonal anti-stem cell factor (SCF) antibody comprising: (a) a light chain variable domain comprising the amino acid sequence of SEQ ID NO:4 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof) identity to SEQ ID NO:4; and (b) a heavy chain variable domain comprising the amino acid sequence of SEQ ID NO:2 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof identity to SEQ ID NO:2. In some embodiments, the light chain variable region has the amino acid sequence of SEQ ID NO:4 and the heavy chain variable region has the amino acid sequence of SEQ ID NO:2. In some embodiment, the antibody is monovalent and comprises an Fc region. In some embodiments, the antibody is bivalent. In some embodiments, the antibody is bispecific. In some embodiments, the antibody is an antibody fragment selected from, for example a Fab, a Fab'-SH, an Fv, an scFv, or a (Fab')$_2$ fragment. In some embodiments, the antibody comprises a single Fab region linked to an Fc region. Antibodies of the invention can further comprise any suitable framework and/or light chain variable domain sequences, provided SCF binding activity is substantially retained. For example, in some embodiments, these antibodies further comprise a human subgroup III heavy chain framework consensus sequence. In one embodiment, these antibodies further comprise a human κI light chain framework consensus sequence.

Further embodiments provide a pharmaceutical composition comprising any of the aforementioned antibodies and a pharmaceutically acceptable carrier.

Additional embodiments provide a nucleic acid encoding any of the aforementioned antibodies. In some embodiments, the nucleic acid comprises a nucleic acid encoding a light chain variable region comprising SEQ ID NO:3 or sequences that are at least 80% (e.g., 81%, 82%, 83%, 84%, 85%, 86%, 87%, 88%, 89%, 90%, 91%, 92%, 93%, 94%, 95%, 96%, 97%, 98%, 99%, or fractions thereof or alternative codons that encode the amino acids of SEQ ID NO:4) homologous to SEQ ID NO:3 and a nucleic acid encoding a heavy chain variable region comprising SEQ ID NO:1 or sequences that are at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof or alternative codons that encode the amino acids of SEQ ID NO:2) homologous to SEQ ID NO:1. In some embodiments, the nucleic acid encoding a light chain variable region comprises SEQ ID NO:3 and the nucleic acid encoding a heavy chain variable region comprises SEQ ID NO:1.

In some embodiments, the present invention provides the use of the aforementioned pharmaceutical composition or antibodies in the treatment of a lung, fibrotic or tissue remodeling disease.

In some embodiments, the present invention provides a method of treating a fibrotic or tissue remodeling disease comprising administering the aforementioned pharmaceutical composition or antibodies to a subject with or at risk for a fibrotic or tissue remodeling disease. In some embodiments, the subject has an abnormal activity of stem cell factor or abnormal collagen production. In some embodiments, the disease is fibrosis, a remodeling disease, or a pulmonary disease (e.g., idiopathic pulmonary fibrosis, chronic obstructive pulmonary disease, acute respiratory distress syndrome, cystic fibrosis, peribronchial fibrosis, hypersensitivity pneumonitis, asthma, pulmonary arterial hypertension (PAH), sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, or radiation-induced fibrosis). In some embodiments, the pharmaceutical composition is delivered into an airway of the subject by e.g., intranasal or inhalational (e.g. dry powder or nebulizer) administration. In some embodiments, the administering reduces an activity of a receptor and/or reduces an interaction of stem cell factor with a receptor (e.g., a receptor tyrosine kinase such as c-Kit). In some embodiments, the administering results in a direct inhibition of fibroblast activation. In some embodiments, the administering results in inhibition of progression of signs or symptoms of a disease.

Additional embodiments will be apparent to persons skilled in the relevant art based on the teachings contained herein.

DESCRIPTION OF THE FIGURES

FIG. 1 shows exemplary CDR and Framework regions of the antibodies of embodiments of the present disclosure.

DETAILED DESCRIPTION

Provided herein are methods, compositions, and uses relating to inhibitors of stem cell factor. For example, provided herein are antibodies targeting stem cell factor, methods of producing antibodies targeting stem cell factor, and methods for treating fibrotic and tissue remodeling diseases as well as for research and diagnostic uses. In some embodiments, the compositions, methods, and uses herein provide therapies relating to inhibiting stem cell factor (SCF). Some embodiments provide an isolated antibody that targets SCF. In some embodiments, inhibiting SCF affects the activity of c-Kit. The compositions, methods, and uses provided herein find use in treating fibrotic diseases and maladies associated with tissue remodeling.

Definitions

To facilitate an understanding of embodiments of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "nascent" when used in reference to a protein refers to a newly synthesized protein, which has not been subject to post-translational modifications, which includes but is not limited to glycosylation and polypeptide shortening. The term "mature" when used in reference to a protein refers to a protein which has been subject to post-translational processing and/or which is in a cellular location (such as within a membrane or a multi-molecular complex) from which it can perform a particular function which it could not if it were not in the location.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include the transmembrane domains, and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors can contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule. In some embodiments, recombinant nucleic acids are in an expression vector (e.g., plasmid), optionally joined to nucleic acids useful for driving expression of the nucleic acid (e.g., promoter or enhancer sequences).

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type"

when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "isolated" when used in relation to a nucleic acid or polypeptide, refers to a nucleic acid or polypeptide that is substantially free of other proteins or nucleic acids (e.g., suitable for pharmaceutical administration).

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used. Specific illustrative embodiments are described in the following.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, "inhibitor" refers to a molecule which eliminates, minimizes, or decreases the activity, e.g., the biological, enzymatic, chemical, or immunological activity, of a target.

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, inflammation, etc.).

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, the term "treating" includes reducing or alleviating at least one adverse effect, sign, or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive vs. conventional treatment).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "pharmaceutical composition" refers to the combination of an active agent with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject.

As used herein, "carriers" include pharmaceutically acceptable carriers, excipients, or stabilizers which are non-toxic to the cell or mammal being exposed thereto at the dosages and concentrations employed. Often the physiologically acceptable carrier is an aqueous pH-buffered solution.

Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "patient" or "subject" refer to organisms to be treated by the compositions of the present technology or to be subject to various tests provided by the technology. The term "subject" includes animals, preferably mammals, including humans. In a preferred embodiment, the subject is a primate. In an even more preferred embodiment, the subject is a human. In some embodiments, the subject is a companion animal (e.g., dog, cats, etc.), an agricultural animal (e.g., cow, sheep, goat, pig, etc.), or an equine.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

Embodiments of the Technology

Although the disclosure herein refers to certain illustrated embodiments, it is to be understood that these embodiments are presented by way of example and not by way of limitation.

1. Inhibitors of SCF

Stem cell factor (SCF) is a ligand that is specific for the c-Kit receptor kinase. Binding of SCF to c-Kit causes dimerization of c-Kit and activation of its kinase activity, which is important for hemopoiesis, melanogenesis, and fertility. Through c-Kit, SCF acts to promote cell survival, proliferation, differentiation, adhesion, and functional activation. Aberrant activation of c-Kit can result in disease, including fibrosis and tissue remodeling defects. In particular, there are multiple pulmonary diseases with known remodeling defects as well as other chronic tissue remodeling diseases affecting other organs and tissues. Specific examples of diseases involving fibrosis or tissue remodeling defects are idiopathic pulmonary fibrosis, chronic obstructive pulmonary disease, pulmonary arterial hypertension (PAH), asthma, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Accordingly, interfering with the interaction between SCF and c-Kit can be used to treat or study diseases involving aberrant activation of c-Kit that causes fibrosis and tissue remodeling defects. The c-Kit receptor is found on hematopoietic progenitor cells, melanocytes, germ cells, eosinophils, lymphocytes, and mast cells. Thus, preventing SCF interaction with c-Kit can alter the activation of several disease-associated cell populations that have been implicated in fibrosis and tissue remodeling disease phenotypes.

Additionally, SCF induces key mediators in the fibrotic response, IL-25 and IL-13. Data suggest that IL-25 can drive IL-13 expression in a T-cell and antigen-independent manner. Therefore, these processes can progress without an antigen-specific response and consequently chronically perpetuate remodeling and fibrotic disease. It is contemplated that a complex cascade is established in which SCF induces IL-25, which in turn induces production of IL-13, myofibroblast differentiation, and collagen production. IL-4 has also been identified as a fibrosis-associated cytokine.

2. Antibodies

In some embodiments, inhibiting the ability of SCF to interact with c-Kit is accomplished by means of an antibody that recognizes SCF. In some embodiments, the antibody is a recombinant antibody (See e.g., Example 1).

It is contemplated that antibodies against SCF find use in the experimental, diagnostic, and therapeutic methods described herein. In certain embodiments, the antibodies provided herein are used to detect the expression of SCF in biological samples. For example, a sample comprising a tissue biopsy can be sectioned and protein detected using, for example, immunofluorescence or immunohistochemistry. Alternatively, individual cells from a sample can be isolated, and protein expression detected on fixed or live cells by FACS analysis. Furthermore, the antibodies can be used on protein arrays to detect expression of SCF. In other embodiments, the antibodies provided herein are used to decrease the activity of cells expressing c-Kit by inhibiting SCF either in an in vitro cell-based assay or in an in vivo animal model. In some embodiments, antibodies are used to treat a subject (e.g., human patient) by administering a therapeutically effective amount of an antibody against SCF.

In some embodiments, the present disclosure provides antibodies having the sequences of SEQ ID NOs:1-4 and variants thereof. For example, in some embodiments, the light chain variable domain comprises the amino acid sequence of SEQ ID NO:4 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof) identity to SEQ ID NO:4; and the heavy chain variable domain comprises the amino acid sequence of SEQ ID NO:2 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof identity to SEQ ID NO:2. In some embodiments, the light chain variable region is encoded by the nucleic acid of SEQ ID NO:3 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof) homology to SEQ ID NO:3. In some embodiments, the heavy chain variable region is encoded by the nucleic acid of SEQ ID NO:1 or sequences with at least 80% (e.g., 81%, 82%, 83%, 84%, 85%, 86%, 87%, 88%, 89%, 90%, 91%, 92%, 93%, 94%, 95%, 96%, 97%, 98%, 99% or fractions thereof) homology to SEQ ID NO:1.

In certain embodiments, antibodies are engineered, for example by including modifications of the Fc region which can alter serum half-life, complement fixation, Fc receptor binding and/or antigen dependent cellular cytotoxicity.

In some embodiments, modified or variant antibodies as described herein retain binding affinity to SCF (e.g., within 10%, 5%, 4%, 3%, 2%, or 1%) of the unmodified antibody.

In some embodiments, binding affinity is increased or decreased relative to the wild-type or unmodified antibody.

In certain embodiments, modifications in the biological properties of an antibody (e.g., those described herein) are accomplished by selecting substitutions that affect (a) the structure of the polypeptide backbone in the area of the substitution, for example, as a sheet or helical conformation, (b) the charge or hydrophobicity of the molecule at the target. The polynucleotide encoding a monoclonal antibody can further be modified in a site, or (C) the bulk of the side chain. Amino acids may be grouped according to similarities in the properties of their side chains (A. L. Lehninger, in Biochemistry, 2nd Ed., 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, He; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Such substituted residues also may be introduced into the conservative substitution sites or, into the remaining (e.g., non-conserved) sites in a number of different manners using recombinant DNA.

In some embodiments, antibodies or antibody fragments are provided that can be produced which have altered glycosylation patterns. In certain embodiments, an antibody is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

In some embodiments, the antibodies are PEGylated by reacting the antibody with a polyethylene glycol (PEG) derivative. In certain embodiments, the antibody is defucosylated and therefore lacks fucose residues.

In some embodiments, humanized anti-SCF antibodies are generated. For example, also contemplated are chimeric mouse-human monoclonal antibodies, which are produced by recombinant DNA techniques known in the art. For example, a gene encoding the constant region of a murine (or other species) monoclonal antibody molecule is digested with restriction enzymes to remove the region encoding the murine constant region, and the equivalent portion of a gene encoding a human constant region is substituted (see, e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 (each of which is herein incorporated by reference in its entirety); Better et al., Science, 240:1041-1043 (1988); Liu et al., Proc. Nat. Acad. Sci. USA, 84:3439-3443 (1987); Liu et al., J. Immunol., 139:3521-3526 (1987); Sun et al., Proc. Nat. Acad. Sci. USA, 84:214-218 (1987); Nishimura et al., Canc. Res., 47:999-1005 (1987); Wood et al., Nature, 314:446-449 (1985); and Shaw et al., J. Natl. Cancer Inst., 80:1553-1559 (1988)).

The chimeric antibody can be further humanized by replacing sequences of the variable region that are not directly involved in antigen binding with equivalent sequences from human variable regions. General reviews of humanized chimeric antibodies are provided by S. L. Morrison, Science, 229:1202-1207 (1985) and by Oi et al., Bio Techniques, 4:214 (1986). Those methods include isolating, manipulating, and expressing the nucleic acid sequences that encode all or part of immunoglobulin variable regions from at least one of a heavy or light chain. Sources of such nucleic acid are well known to those skilled in the art. The recombinant DNA encoding the chimeric antibody, or fragment thereof, can then be cloned into an appropriate expression vector.

Suitable humanized antibodies can alternatively be produced by CDR substitution (see, e.g., U.S. Pat. No. 5,225,539; Jones et al., Nature, 321:552-525 (1986); Verhoeyan et al., Science, 239:1534 (1988); and Beidler et al., J. Immunol., 141:4053 (1988)). All of the CDRs of a particular human antibody may be replaced with at least a portion of a non-human CDR or only some of the CDRs may be replaced with non-human CDRs. It is only necessary to replace the number of CDRs important for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs using oligonucleotide site-directed mutagenesis.

A humanized antibody may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody comprises a human consensus framework sequence, which in one embodiment is the subgroup III consensus framework sequence. In one embodiment, an antibody comprises a variant subgroup III consensus framework sequence modified at least one amino acid position. In one embodiment, the light chain variable domain of an antibody comprises a human consensus framework sequence, which in one embodiment is the κI consensus framework sequence. In one embodiment, an antibody comprises a variant κI consensus framework sequenced modified at least one amino acid position.

As is known in the art, and as described in greater detail herein below, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). Embodiments of the invention provide antibodies comprising modifications in these hybrid hypervariable positions. In one embodiment, an antibody comprises a human variant human subgroup consensus framework sequence modified at one or more hybrid hypervariable positions.

An antibody as described herein can comprise any suitable human or human consensus light chain framework sequences, provided the antibody exhibits the desired biological characteristics (e.g., a desired binding affinity). In one embodiment, an antibody of embodiments of the disclosure comprises at least a portion (or all) of the framework sequence of human κ light chain. In one embodiment, an antibody of embodiments of the disclosure comprises at least a portion (or all) of human kappa subgroup I framework consensus sequence.

In some embodiments, antibodies are humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also comprises at least a portion of an immunoglobulin constant region (Fc), typically that of a human immunoglobulin (Jones et al., Nature, 321:522-525 (1986); Riechmann et al., Nature, 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important to reduce antigenicity and HAMA response (human anti-mouse antibody) when the antibody is intended for human therapeutic use. Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, in some embodiments, the invention provides antibodies that are humanized. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

While the acceptor may be identical in sequence to the human framework sequence selected, whether that be from a human immunoglobulin or a human consensus framework, embodiments of the present invention contemplate that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35B (H1), 50-65, 47-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., Proteins, 8:309 (1990); Lowman and Wells, Methods: A Companion to Methods in Enzymology, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. Nos. 5,723,286, 5,432,018, 5,580,717, 5,427,908 and 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Additional methods of preparing and screening libraries are described, for example, in Geyer et al., Methods Mol Biol. 2012; 901:11-32; and de Marco A. Crit Rev Biotechnol. 2013 March; 33(1):40-8; each of which is herein incorporated by reference in its entirety.

Methods of substituting an amino acid of choice into a template nucleic acid are well established in the art, some of which are described herein. For example, hypervariable region residues can be substituted using the Kunkel method. See, e.g., Kunkel et al., Methods Enzymol. 154:367-382 (1987).

According to another method, antigen binding may be restored during humanization of antibodies through the selection of repaired hypervariable regions (See US20060122377). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps are isolated and cloned using standard recombinant techniques. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody has an affinity that is "3-fold lower" than the affinity of a reference antibody (M), then if the Kd value for A is 3x, the Kd value of M would be 1x, and the ratio of Kd of A to Kd of M would be 3:1. Conversely, in one embodiment, if an antibody has an affinity that is "3-fold greater" than the affinity of a reference antibody (R), then if the Kd value for C is 1x, the Kd value of R would be 3x, and the ratio of Kd of C to Kd of R would be 1:3. Any of a number of assays known in the art, including those described herein, are used to obtain binding affinity measurements, including, for example, Biacore, radioimmunoassay (RIA) and ELISA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

It may be desirable to modify the antibody with respect to effector function, e.g., so as to enhance or decrease antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

DNA encoding the Fv clones can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

It is further useful that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Also contemplated are chimeric and humanized antibodies in which specific amino acids have been substituted, deleted, or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In certain embodiments provided herein, it is desirable to use an antibody fragment. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). For example, papain digestion of antibodies produces two identical antigen-binding fragments, called Fab fragments, each with a single antigen-binding site, and a residual Fc fragment. Pepsin treatment yields an $F(ab')_2$ fragment that has two antigen-combining sites and is still capable of cross-linking antigen.

However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

Fv is the minimum antibody fragment which contains a complete antigen-recognition and antigen-binding site. This region consists of a dimer of one heavy-chain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. $F(ab')_2$ antibody fragments originally were produced as pairs of Fab' fragments which have hinge cysteines between them. Other chemical couplings of antibody fragments are also known to the skilled artisan.

The technology herein provided also contemplates modifying an antibody to increase its serum half-life. This can be achieved, for example, by incorporating a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The technology embraces variants and equivalents which are substantially homologous to the chimeric, humanized, and human antibodies, or antibody fragments thereof, provided herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

An additional embodiment utilizes the techniques known in the art for the construction of Fab expression libraries (Huse et al., Science, 246:1275-1281 (1989)) to allow rapid and easy identification of monoclonal Fab fragments with the desired specificity.

Also, this technology encompasses bispecific antibodies that specifically recognize SCF. Bispecific antibodies are antibodies that are capable of specifically recognizing and binding at least two different epitopes. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

Techniques described for the production of single chain antibodies (U.S. Pat. No. 4,946,778; herein incorporated by reference) can be adapted to produce specific single chain antibodies as desired. Single-chain Fv antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the single-chain Fv antibody fragments to form the desired structure for antigen binding. For a review of single-chain Fv antibody fragments, see Pluckthun in The Pharmacology of Monoclonal Antibodies, vol. 113, Rosenburg and Moore eds., Springer-Verlag, New York, pp. 269-315 (1994).

Antibodies with the desired properties can be generated and purified using any suitable method. In some embodiments, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography.

Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In some embodiments, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters. Medium scale reactors are reactors of 100 L-1000 L.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system.

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

2. Therapies Using Inhibitors of SCF

Inhibiting SCF finds use in therapies to treat disease. Accordingly, provided herein are therapies comprising inhibiting SCF to benefit individuals suffering from disease. In particular, as shown herein, disease states involving fibrosis and tissue remodeling demonstrate aberrant SCF activity. For example, fibroblasts isolated from diseased individuals with fibrotic or tissue remodeling phenotypes directly respond to SCF, which results in the generation of a more severe phenotype that includes increased collagen production. As such, as shown herein, inhibiting SCF can significantly affect the generation of severe disease consequences including inflammation and remodeling of target tissue. Also contemplated are therapies targeting SCF during the generation of fibrosis associated with acute and chronic disorders that have either a dynamic disease course or a more predictable disease course. Indications that can benefit from therapy inhibiting SCF include, but are not limited to, idiopathic pulmonary fibrosis, pulmonary arterial hypertension (PAH), chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Importantly, therapies targeting SCF reduce or eliminate toxic effects associated with other similar therapies, for example those targeting c-Kit. These undesirable toxic effects are associated with targeting an intracellular, rather than extracellular, target, and the more widespread and general changes in cell signaling that result. While the therapies are not limited in their route of administration, embodiments of the technology provided herein deliver the SCF inhibitor via the airway by intranasal administration. Such administration allows direct delivery of the therapeutic agent to target tissues in pulmonary diseases involving fibrosis and tissue remodeling, rather than relying on systemic delivery via an orally administered composition.

In certain embodiments, a physiologically appropriate solution containing an effective concentration of an antibody specific for SCF can be administered topically, intraocularly, parenterally, orally, intranasally, intravenously, intramuscularly, subcutaneously, or by any other effective means. In particular, the antibody may delivered into an airway of a subject by intranasal administration. Alternatively, a tissue can receive a physiologically appropriate composition (e.g., a solution such as a saline or phosphate buffer, a suspension, or an emulsion, which is sterile) containing an effective concentration of an antibody specific for SCF via direct injection with a needle or via a catheter or other delivery tube. Any effective imaging device such as X-ray, sonogram, or fiber-optic visualization system may be used to locate the target tissue and guide the administration. In another alternative, a physiologically appropriate solution containing an effective concentration of an antibody specific for SCF can be administered systemically into the blood circulation to treat tissue that cannot be directly reached or anatomically isolated. Such manipulations have in common the goal of placing an effective concentration of an antibody specific for SCF in sufficient contact with the target tissue to permit the antibody specific for SCF to contact the tissue.

With respect to administration of a SCF inhibitor (e.g., an antibody specific for SCF) to a subject, it is contemplated that the SCF inhibitor be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

In some embodiments, a SCF inhibitor (e.g., an antibody specific for SCF) according to the technology provided herein is administered in a pharmaceutically effective amount. In some embodiments, a SCF inhibitor (e.g., an antibody specific for SCF) is administered in a therapeutically effective dose. The dosage amount and frequency are selected to create an effective level of the SCF inhibitor without substantially harmful effects. When administered, the dosage of a SCF inhibitor (e.g., an antibody specific for SCF) will generally range from 0.001 to 10,000 mg/kg/day or dose (e.g., 0.01 to 1000 mg/kg/day or dose; 0.1 to 100 mg/kg/day or dose).

Pharmaceutical compositions preferably comprise one or more antibodies as described herein associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro ed., 1985).

For administration by inhalation, the compounds are delivered in the form of an aerosol spray or dry powder from pressured container or dispenser which contains a suitable propellant, e.g., a gas such as carbon dioxide, or a nebulizer. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In some embodiments, a single dose of a SCF inhibitor (e.g., an antibody specific for SCF) according to the technology provided herein is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years; e.g., for the lifetime of the subject). In such embodiments, compounds may be taken on a regular scheduled basis (e.g., daily, weekly, etc.) for the duration of the extended period.

In some embodiments, a SCF inhibitor (e.g., an antibody specific for SCF) according to the technology provided herein is co-administered with another compound or more than one other compound (e.g., 2 or 3 or more other compounds). Examples include, but are not limited to, immunosuppressive therapy such as corticosteroids and immunosuppressants, such as cyclophosphamide, azathioprine, methotrexate, penicillamine, and cyclosporine.

3. Kits

Some embodiments provide herein kits for the treatment of a subject. In some embodiments, the kits include an antibody that binds to SCF and appropriate solutions and buffers. Embodiments include all controls and instructions for use. In some embodiments, kits include delivery systems (e.g., injectors, inhalers, nebulizers, etc.).

EXAMPLES

Example 1

Isolation and Sequencing of Monoclonal Antibodies to SCF

A. Methods

Total RNA was extracted from fresh hybridoma cells recovered by GenScript and cDNA was synthesized from the RNA. RT-PCR was then performed to amplify the variable regions (heavy and light chains) of the antibody, which were then cloned into a standard cloning vector separately and sequenced.

Hybridoma cells recovered by GenScript; TRIzol® Plus RNA Purification System (Invitrogen, Cat. No.: 15596-026); SuperScript™ III First-Strand Synthesis System (Invitrogen, Cat. No.: 18080-051).

Total RNA was isolated from the hybridoma cells following the technical manual of TRIzol® Plus RNA Purification System. The total RNA was analyzed by agarose gel electrophoresis.

Total RNA was reverse transcribed into cDNA using isotype-specific anti-sense primers or universal primers following the technical manual of SuperScript™ III First-Strand Synthesis System. The antibody fragments of VH and VL were amplified according to the standard operating procedure of RACE of GenScript.

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

B. Results

Five single colonies with correct VH and VL insert sizes were sequenced. The VH and VL genes of five different clones were found nearly identical. The consensus sequence, listed below, is the sequence of the antibody produced by the hybridoma 2G8D3.

Heavy chain: DNA sequence
(402 bp; SEQ ID NO: 1)
Leader sequence-FR1-CDR1-FR2-CDR2-FR3-CDR3-FR4
ATGGACAGGCTTACTTCTTCATTCCTGCTGCTGATTGTCCCTGCATATGT

CTTATCCCAAGTTTCTCTAAAAGAGTCTGGCCCTGGGATATTGAGGCCCT

CACAGACCCTCATTCTGACTTGTTCTTTCTCTGGGTTTTCACTGAGTACT

TCTGGTATGGGTGTGGGCTGGATTCGTCAGCCTTCAGGGAAGGGTCTGGA

GTGGCTGGCACACATTTGGTGGGATGATGAGAAGTCCTATAACCCATCCC

TGAAGAGCCGGCTCACGATCTCCAAGGATGCCTCCCGAGACCAGGTTTTC

CTCAAGATCACCAATGTGGACACTACAGATACTGCCACTTACTTCTGTGC

TCGAAGCGGCTTGGACTACGGGGTCAAGGAATTTCAGTCACCGTCTCCT

CA

Heavy chain: Amino acids sequence
(134 AA; SEQ ID NO: 2)
Leader sequence-FR1-CDR1-FR2-CDR2-FR3-CDR3-FR4
MDRLTSSFLLLIVPAYVLSQVSLKESGPGILRPSQTLILTCSFSGFSLST
SGMGVGWIRQPSGKGLEWLAHIWWDDEKSYNPSLKSRLTISKDASRDQVF
LKITNVDTTDTATYFCARSGLDYWGQGISVTVSS Light chain: DNA sequence
(402 bp; SEQ ID NO: 3)
Leader sequence-FR1-CDR1-FR2-CDR2-FR3-CDR3-FR4
ATGGCCTGGACTCCTCTCTTCTTCTTTCTTTGTTCTTCATTGCTCAGGTTC

TTTCTCCCAACCTGTGCTCACTCAGTCATCTTCAGCCTCTTTCTCCCTGG

GAGCCTCAGCAAAAATCACGTGCACCTTGAGTAGTCAGCACAGGACGTAC

ACCATTGAATGGTATCAGCAACAGCCACTCAAGCCTCCTAAGTATGTGAT

GGAACTTAAGAGAGATGGAAGTCACAGAACAGGTGATGGGATTCCTGATC

GCTTCTCTGGATCCAGCTCTGGTGCTGATCGCTACCTAACCATTGCCAAC

ATCCAGCCTGAAGATGAAGCAATGTACATCTGTGGTGCTGATGATACAAT

TCAGGAACAATTTGTGTATGTTTTCGGCGGTGGAACCAAAGTCACTGTCC

TC

Light chain: Amino acids sequence
(134 AA; SEQ ID NO: 4)
Leader sequence-FR1-CDR1-FR2-CDR2-FR3-CDR3-FR4
MAWTPLFFFFVLHCSGSFSQPVLTQSSSASFSLGASAKITCTLSSQHRTY
TIEWYQQQPLKPPKYVMELKRDGSHRTGDGIPDRFSGSSSGADRYLTIAN
IQPEDEAMYICGADDTIQEQFVYVFGGGTKVTVL All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. An isolated recombinant monoclonal anti-stem cell factor (SCF) antibody comprising:
   (a) a light chain variable domain comprising an amino acid sequence comprising:
      (i) a first amino acid sequence comprising the CDR1 sequence provided by amino acids 42-53 of SEQ ID NO: 4;
      a second amino acid sequence comprising the CDR2 sequence provided by amino acids 69-79 of SEQ ID NO: 4; and
      (iii) a third amino acid sequence comprising the CDR3 sequence provided by amino acids 112-124 of SEQ ID NO: 4; and
   (b) a heavy chain variable domain comprising an amino acid sequence comprising:
      (i) a first amino acid sequence comprising the CDR1 sequence provided by amino acids 45-56 of SEQ ID NO: 2;
      a second amino acid sequence comprising the CDR2 sequence provided by amino acids 71-86 of SEQ ID NO: 2; and
      (iii) a third amino acid sequence comprising the CDR3 sequence provided by amino acids 119-123 of SEQ ID NO: 2.

2. The antibody of claim 1, wherein the antibody is a humanized antibody.

3. The antibody of claim 1, wherein the antibody is a chimeric antibody.

4. The antibody of claim 1, wherein the antibody is monovalent and comprises an Fc region.

5. The antibody of claim 1, wherein the antibody is bivalent or bispecific.

6. The antibody of claim 1, wherein the antibody is an antibody fragment selected from the group consisting of a Fab, a Fab'-SH, an Fv, an scFv, and a (Fab')₂.

7. The antibody of claim 1, wherein the antibody comprises a single Fab region linked to an Fc region.

* * * * *

UNITED STATES PATENT AND TRADEMARK OFFICE
CERTIFICATE OF CORRECTION

PATENT NO. : 10,501,535 B2
APPLICATION NO. : 15/163391
DATED : December 10, 2019
INVENTOR(S) : Nicholas W. Lukacs, Steven L. Kunkel and Cory Hogaboam Page 1 of 1

It is certified that error appears in the above-identified patent and that said Letters Patent is hereby corrected as shown below:

In the Claims

Claim 1, Column 27, Line 44 reads:
"a second amino acid sequence comprising the CDR2"

Whereas it should read:
"(ii) a second amino acid sequence comprising the CDR2"

Claim 1, Column 28, Line 36 reads:
"a second amino acid sequence comprising the CDR2"

Whereas it should read:
"(ii) a second amino acid sequence comprising the CDR2"

Signed and Sealed this
First Day of December, 2020

Andrei Iancu
*Director of the United States Patent and Trademark Office*